US008686360B2

(12) United States Patent
Ohnishi

(10) Patent No.: US 8,686,360 B2
(45) Date of Patent: Apr. 1, 2014

(54) MICRO-SAMPLE PROCESSING METHOD, OBSERVATION METHOD AND APPARATUS

(75) Inventor: Tsuyoshi Ohnishi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 400 days.

(21) Appl. No.: 12/963,201

(22) Filed: Dec. 8, 2010

(65) Prior Publication Data

US 2011/0073758 A1 Mar. 31, 2011

Related U.S. Application Data

(62) Division of application No. 12/121,466, filed on May 15, 2008, now Pat. No. 7,872,230.

(30) Foreign Application Priority Data

May 18, 2007 (JP) ................................. 2007-132281

(51) Int. Cl.
H01J 37/26 (2006.01)
(52) U.S. Cl.
CPC ...................................... H01J 37/26 (2013.01)
USPC ............................. 250/309; 250/306; 250/310
(58) Field of Classification Search
USPC ..................... 250/309, 492.21, 306, 310, 311
See application file for complete search history.

(56) References Cited

U.S. PATENT DOCUMENTS 5,532,494 A * 7/1996 Kawanami et al. ......... 250/491.1
6,627,889 B2 * 9/2003 Ochiai et al. ...................... 850/9

(Continued)

FOREIGN PATENT DOCUMENTS

JP 05-052721 3/1993
JP 11-219680 A 8/1999

(Continued)

OTHER PUBLICATIONS

Japanese Office Action issued in Japanese Patent Application No. 2007-132281, dated Jul. 12, 2011.

(Continued)

*Primary Examiner* — Kiet T Nguyen
(74) *Attorney, Agent, or Firm* — McDermott Will & Emery LLP

(57) ABSTRACT

As sample sizes have decreased to microscopic levels, it has become desirable to establish a method for thin film processing and observation with a high level of positional accuracy, especially for materials which are vulnerable to electron beam irradiation. The technological problem is to judge a point at which to end FIB processing and perform control so that the portion to be observed ends up in a central portion of the thin film. The present invention enables display of structure in cross-section by setting a strip-like processing region in an inclined portion of a sample cross-section and enlarging the display of the strip-like processing region on a processing monitor in a short-side direction. It is then possible to check the cross-sectional structure without additional use of an electron beam. Since it is possible to check the processed section without using an electron beam, electron beam-generated damage or deformation to the processed section is avoided. Further, performing the observation using a high-speed electron beam after forming the thin film enables observation with suppressed sample damage. Processing of even thinner thin films using the FIB while observing images of the sample generated using an electron beam is then possible.

3 Claims, 11 Drawing Sheets

(56) References Cited

U.S. PATENT DOCUMENTS

| | | |
|---|---|---|
| 7,442,928 B2 * | 10/2008 | Ohnishi .................... 250/309 |
| 7,459,699 B2 | 12/2008 | Kiyohara et al. |
| 2004/0262516 A1 | 12/2004 | Motoi et al. |

FOREIGN PATENT DOCUMENTS

| | | |
|---|---|---|
| JP | 2000-147070 A | 5/2000 |
| JP | 2003-194746 A | 7/2003 |
| JP | 2007-109560 A | 4/2007 |
| JP | 2008-520066 | 6/2008 |
| WO | WO 2006/050613 A1 | 5/2006 |

OTHER PUBLICATIONS

Entire Prosecution of U.S. Appl. No. 12/121,466 to Ohnishi, filed May 15, 2008 entitled "Micro-Sample Processing Method, Observation Method and Apparatus".

* cited by examiner (a)

(b)

(a)

(b)

MICRO-SAMPLE PROCESSING METHOD, OBSERVATION METHOD AND APPARATUS

RELATED APPLICATIONS

This application is a Divisional of U.S. patent application Ser. No. 12/121,466, filed on May 15, 2008 now U.S. Pat. No. 7,872,230, claiming priority of Japanese Application No. 2007-132281, filed on May 18, 2007, the entire contents of each of which are hereby incorporated by reference.

BACKGROUND OF THE INVENTION

1. Field of the Invention

The present invention relates to a micro-sample processing and observation technology using a focused ion beam.

2. Background Art

With the micronization of semiconductors, the need to observe and analyze microstructures has greatly increased. Focused Ion Beam (hereinafter abbreviated to FIB) apparatuses are capable of processing micro-samples, and can therefore be used, in particular, as sample pre-processing apparatuses for apparatuses capable of observing micro-samples, such as Scanning Electron Microscopes (hereinafter abbreviated to SEM), Scanning Transmission Electron Microscopes (hereinafter abbreviated to STEM), and Transmission Electron Microscopes (hereinafter abbreviated to TEM). Since FIB techniques allow the imaging of secondary particles (such as secondary electrons) generated by a sample and the setting of a processing region based on the images, it is possible to form a section at a desired point in the sample, and have a capability which is of great benefit in the diagnosis of faults. Since the micronization of semiconductor structures has proceeded further in recent years, the use of high resolution STEMs or TEMs in the observation of samples has increased. To allow observation by STEMs and TEMs, it is necessary to extract a sample from the substrate and process the extracted sample to a thinness that is transparent to an electron beams. The FIB has various uses in this process.

[Patent Document 1] JP Patent Application (Kokai) No. 5-52721 (1993).

SUMMARY OF THE INVENTION

The technological issue with regard to the micronization of the sample is to judge at what point to end the FIB processing, and to control the processing so that the portion to be observed is left over in the center of the thin film. To realize a solution, a method is now in use whereby an FIB and an SEM are installed in the same sampling chamber, the section being processed by the FIB is observed using the SEM, and the point at which to end the process is judged accordingly. However, to realize microstructures having special electrical properties materials which are extremely sensitive to electron beam radiation, known as low-k materials, are widely used, and consequently there are many instances where sample broken or deformed by the SEM observation. Various methods have been considered and tested as ways to prevent such damage. These include (1) reducing the amount of damage by cooling the sample, and (2) dramatically reducing the acceleration voltage of the electron beam so as to reduce an irradiation energy. Method (1) has the disadvantage that time is required for cooling and exchanging samples, dramatically reducing throughput of the process. Also, since electron-beam irradiation causes local damage, deformation will occur at the observed portion despite the cooling of the sample stage if the cooling path is insufficiently secure. Method (2) has the disadvantage that the imaging resolution is lower by the reduction in the acceleration voltage of the electron beam, making it difficult to check the microstructure.

The object of the present invention is to implement thin film processing with a high positional accuracy for a sample constructed from a material vulnerable to electron beam radiation while suppressing breakage and deformation, so as to allow observation of the microstructures of the sample.

The present invention relates to the provision of a capability to monitor a cross-sectional structure during FIB processing by making use of secondary particles generated from the sample as a result of the milling of the cross-section instead of an electron beam.

Display of the cross-section microstructure is possible by setting a strip-like processing region at an inclined portion of the sample cross-section, and enlarging the display on the processing monitor in a direction corresponding to a short-side of the strip-like processing region. It is then possible to check the structure of the cross-section without using an electron beam. Since it is possible to check the cross-section being processed without using an electron beam, the damage and deformation which would result from use of an electron beam on the cross-section being processed do not occur. By implementing the observation with a high-acceleration electron beam after creation of the thin film, it is possible to perform the observation with reduced sample damage, and then to fabricate an even thinner film using the FIB while observing a sample image resulting from an electron beam.

According to the present invention, it is possible to perform FIB cross-section processing and thin film processing while suppressing damage and deformation to a sample cross-section. Also, by combining the FIB with a high-acceleration SEM, STEM, and TEM, it is possible to observe the sample in which the damage and deformation have been minimized at a high resolution.

DETAILED DESCRIPTION OF THE PREFERRED EMBODIMENTS

Figure 1:
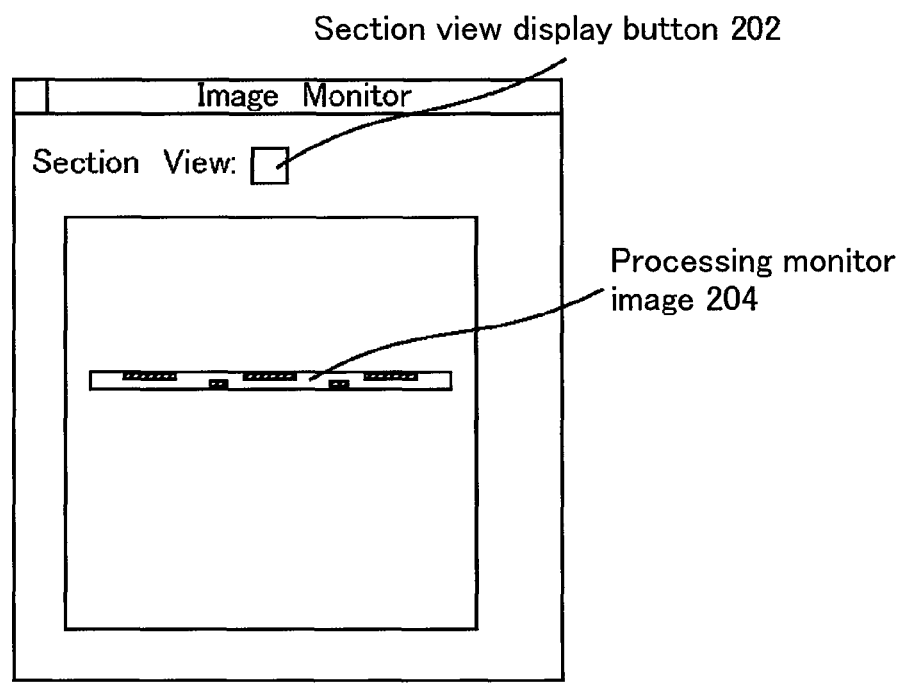
FIG. 1 shows an image monitor window used in a first embodiment of the present invention.
Figure 1:
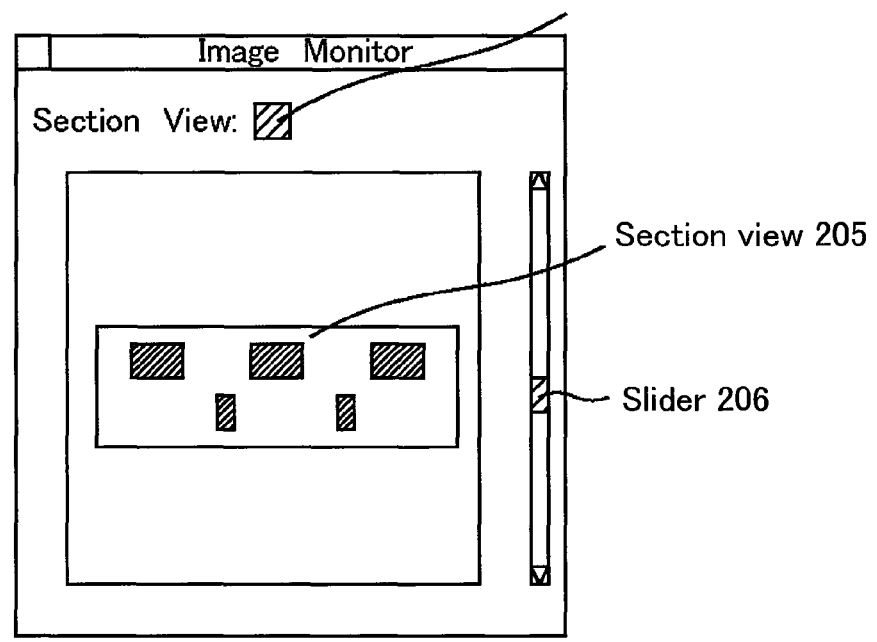

The present invention makes it possible to monitor a cross-sectional structure during FIB processing using a secondary particle image generated from the sample as a result of the milling of the cross-section by FIB rather than as a result of an electron beam.

In a final stage of the milling of the cross-section, the processing region has a long thin strip-like form and the monitor image generally has a strip-like form. The judgment of the end point of the processing using the monitor image was conventionally performed based on an average brightness over the entire monitor. Hence, although it was possible to roughly gain an understanding of a process by which the cross-section processing proceeded from a surface towards a substrate side of the sample, it was difficult to gain an understanding of the structure of the cross-section. For this reason, the use of an SEM has been considered.

In the embodiments, the monitor picture was enlarged in a short-side direction of the strip-like form, making it possible to gain an understanding of the cross-sectional structure as the processing using the FIB alone proceeded.

The processing cross-section generally formed by FIB processing has an inclination of a few degrees relative to the angle of incidence of the ion beam because of a relationship between a local angle of the ion beam incident on the sample and a sputtering yield (J. Vac. Sci. Technol. B9(5). September/October 1991, pp 2636). In the embodiments it is possible to display the structure of the cross-section by making use of this physical phenomenon, setting the strip-like processing region in the inclined portion, and expanding the picture on the process monitor in the short-side direction. Since the beam irradiates from an inclined direction approximately parallel to the cross-section, the image resolution deteriorates more than the beam diameter, but it is possible to display an image of sufficient resolution to roughly gain an understanding of, for instance, whether a wiring structure is present in the cross-section structure. When the section structure is checked using the above-described function and the desired section has not been achieved, the desired cross-section can be achieved by repeatedly shifting the process region in the cross-section direction and making judgments about the cross-section structure. Since it is possible to create the desired section without using the SEM, the method is suitable for samples which are vulnerable to electron beam irradiation.

It is possible to manufacture the thin film sample with a high positional accuracy by applying the above-described method for forming the cross-section to at least one side of the thin film. When the thin film reaches a thickness of approximately 0.3 µm or less, conditions are reached under which an electron beam having an acceleration voltage of 15 kV or more is able to pass through the sample more easily and energy loss in the sample is small, and sample damage consequently becomes less likely. Hence, the sample can be formed into thin film using the FIB alone, and the resulting sample, for which damage and deformation have been suppressed, can be observed using an SEM, STEM, or TEM under high-acceleration conditions.

Also when additional processing is necessary, it is possible to form an even thinner thin film by performing additional FIB processing while monitoring at least one image from an SEM, an STEM, or a TEM under high-acceleration conditions. Since it is possible at this point to perform the monitoring using an electron beam having a high acceleration voltage, the end point of the FIB processing can be judged using a high-resolution image.

The present embodiments makes it possible to monitor the structure of the cross-section during FIB processing using a secondary particle image generated from the sample as a result of FIB milling of the cross-section. By setting a strip-like processing region at an inclined portion of the sample cross-section and enlarging the corresponding monitor picture in the short-side direction, it is possible to display the cross-section structure (section view). When the section structure is checked using the above-described function and the desired cross-section has not been achieved, the desired cross-section can be achieved by repeatedly shifting the processing region in the cross-section direction and making judgments about the cross-section structure. Since it is possible to create the desired cross-section without using the SEM, this method is suitable for processing samples which are vulnerable to electron beam radiation.

It is possible to manufacture the thin film sample with a high positional accuracy by applying the above-described method for forming the cross-section to at least one side of the thin film. By performing the observation using electrons which have been highly accelerated using a voltage of 15 kV or more after forming the thin film, the observation is possible in a manner which suppresses sample damage and deformation. Moreover, by performing further thin film processing while observing images obtained under the above-described conditions, it is possible to produce of a sample which is even thinner with a high degree of positional accuracy, and to observe the sample at high resolutions.

The following describes the embodiments with reference to the drawings.

First Embodiment

Figure 5:
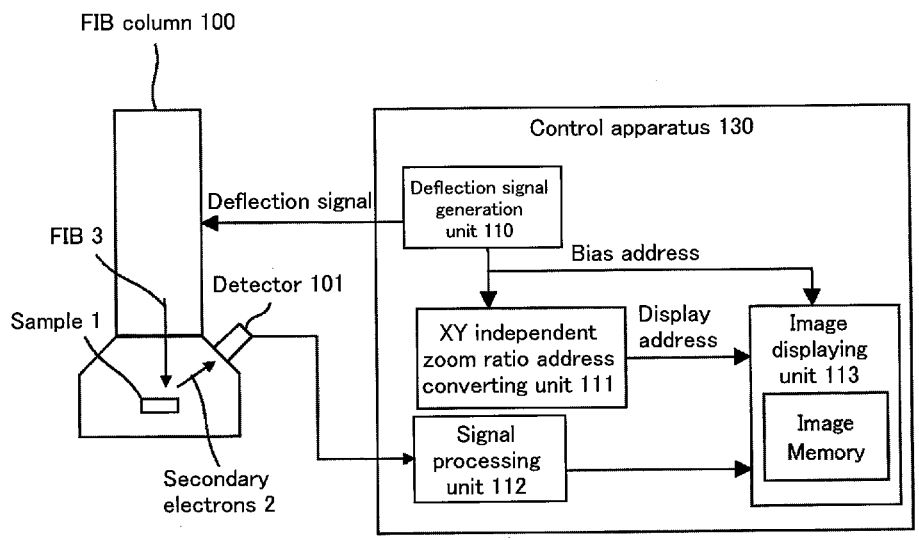
FIG. 5 is a system construction of the FIB apparatus used in the first embodiment of the present invention.

FIG. 5 shows a construction of an FIB apparatus used in a first embodiment of the present invention. An FIB 3 generated by the FIB column 100 is focused on and scanned across a sample 1. Secondary electrons 2 emitted from the sample are detected by a detector 101, converted to digital values via a signal processing unit 112, and stored in an image memory in an image displaying unit 113. The storage to the image memory is controlled using a deflection address from a deflection signal generation unit 110. The apparatus includes an XY independent zoom ratio address converting unit 111, and is capable of altering display ratios for the X and Y axes independently.

Figure 6:
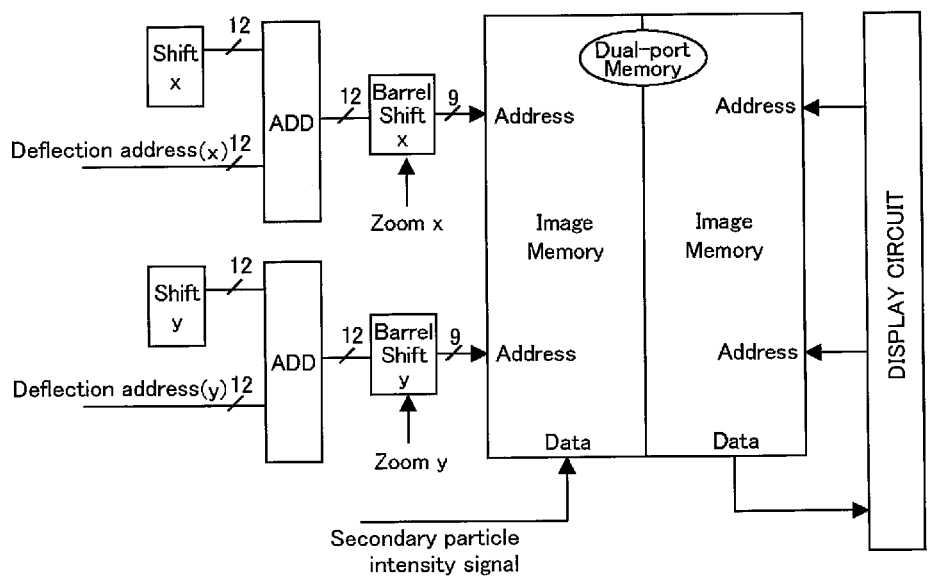
FIG. 6 is a block diagram of an image display circuit used in the first embodiment of the present invention.

FIG. 6 shows circuits surrounding the image memory of the image display unit. Changes to the zoom ratios and the addresses are realized by a digital adder and a barrel shift circuit. Further, a dual port memory which is capable of performing the reading and writing of data is asynchronously used as the image memory.

Figure 2:
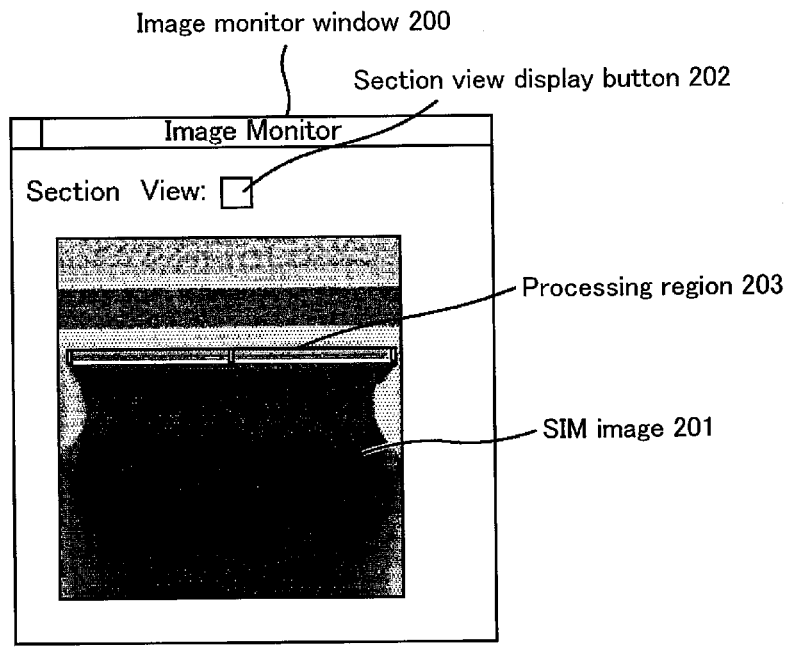
FIG. 2 shows an image monitor window used in the first embodiment of the present invention.
Figure 9:
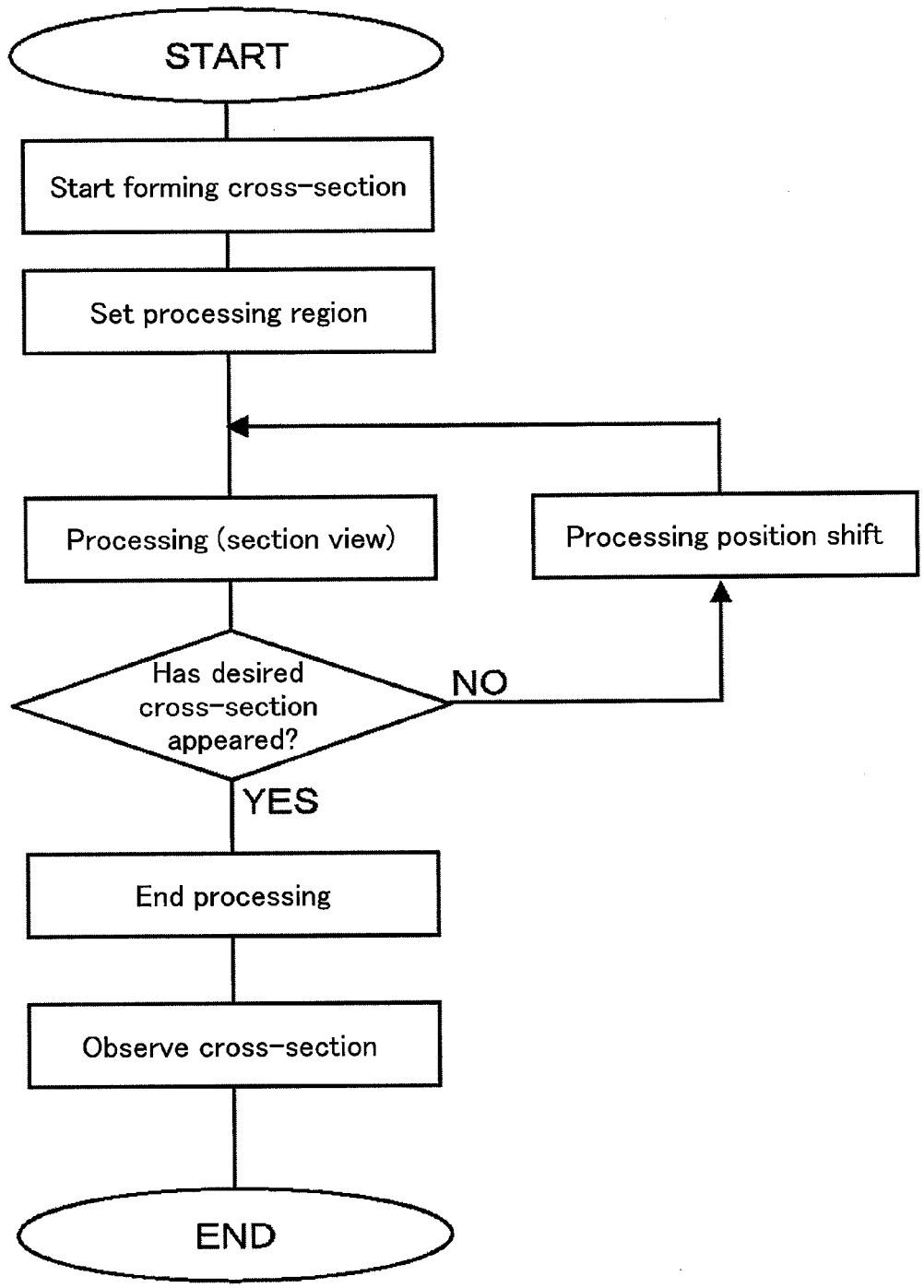
FIG. 9 is a process flowchart used in the first embodiment of the present invention.

FIG. 9 is a flowchart showing a procedure of the first embodiment. First, rectangle processing was performed in the region of a fault to form an initial cross-section. Next, a Scanning Ion Microscope (hereinafter SIM) image 201 was displayed in an image monitor window 200 as shown in FIG. 2, a strip-like processing region 203 was set in a (minutely inclined) cross-sectional portion of the sample, and processing was started. When the processing is started, a processing monitor image 204 is displayed as shown in FIG. 1A. When a cross-section view display button 202 was pressed in the image monitor window 200, the y-axis of the processing monitor was stretched as shown in FIG. 1B, and it became possible to recognize a cross-section structure in the image monitor (section view 205).

Figure 3:
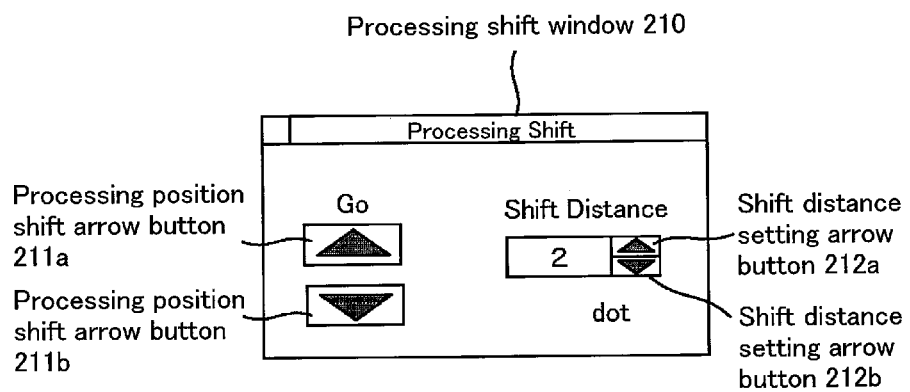
FIG. 3 is a processing shift window used in the first embodiment of the present invention.

Since the desired section was not exposed by the initial processing, a shift amount and a shift direction for the processing region were set using the processing shift window shown in FIG. 3, and the processing position was shifted in a cross-section direction. A shift amount of 2 dots (twice a minimum unit of a processing scanner) was set using a shift distance setting arrow button 212a, and the shift was executed using a processing position shift arrow button 211a. In the present embodiment, an observation and shift in processing position were executed 3 times. It was then possible to confirm that a desired cross-section structure had been realized, and the processing was ended. After completion of the processing, the sample was inclined and an SIM image observation of the cross-section was performed.

Since it is possible, according to the present embodiment, to check the cross-section structure during the processing of the cross-section using the FIB, the sample does not need not be inclined to check each cross-section, and an improvement in efficiency of output and throughput of FIB cross-sections can be achieved. Moreover, in the FIB cross-section processing before observation of the cross-section, observation of the cross-section using an electron beam during the FIB processing is unnecessary, and the processing method can therefore be said to be appropriate for the processing of materials which are vulnerable to electronic beam irradiation. In the present embodiment, the processing region was set to be strip-like in form, but trapezoidal and other forms other than strip-like forms may be used provided that it is possible to realize processing in the region of the cross-section.

Second Embodiment

Figure 4:
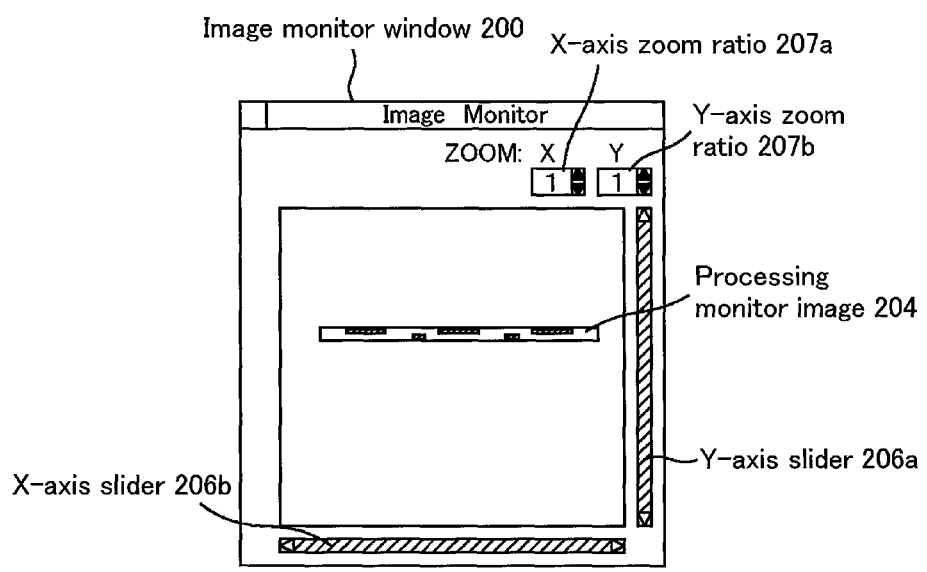
FIG. 4 shows an image monitor window used in a second embodiment of the present invention.
Figure 4:
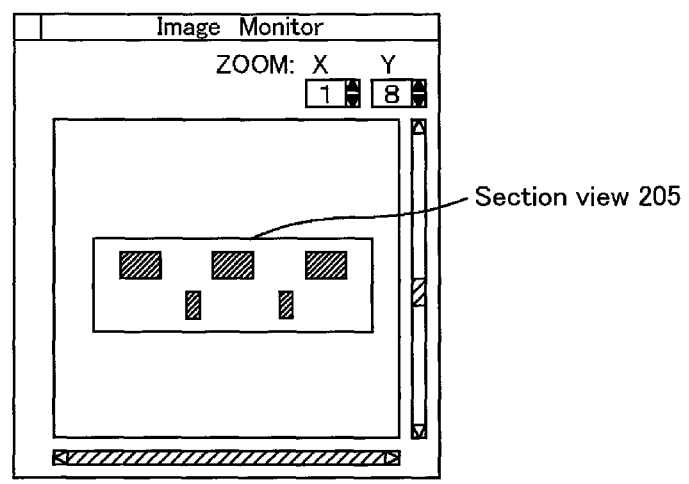

FIG. 4 shows an image monitor window used in a second embodiment. In the second embodiment, the section view function includes a function for expansion of images in the x-direction as well as the function for the expansion of images in the y-direction. Moreover, the respective expansion ratios can be set individually. Hence, the display settings can be finely adjusted to match the sample, and judgments about the processing cross-section are simplified.

FIG. 4A shows the operation state of the standard processing monitor when the zoom ratios are "1" for both the x-direction and the y-direction. FIG. 4B shows the same section view display as in the first embodiment but with a y-axis zoom ratio of "8".

Third Embodiment

The third embodiment describes an example in which the manufacture and observation of a thin-film sample are performed. The apparatus which was used is a compound apparatus having an FIB column 100 and an SEM column 150 installed in a same sample chamber. A gas source 170 for performing beam induced deposition and a manipulator 140 for handling the micro-samples are also installed in the sample chamber. Moreover, a large-sample stage 160 for holding and moving a sample 1 is installed in the sample chamber. Besides the sample 1, a thin-film carrier 10 for mounting the micro-sample obtained by the sampling is also mounted on the sample stage.

Figure 8:
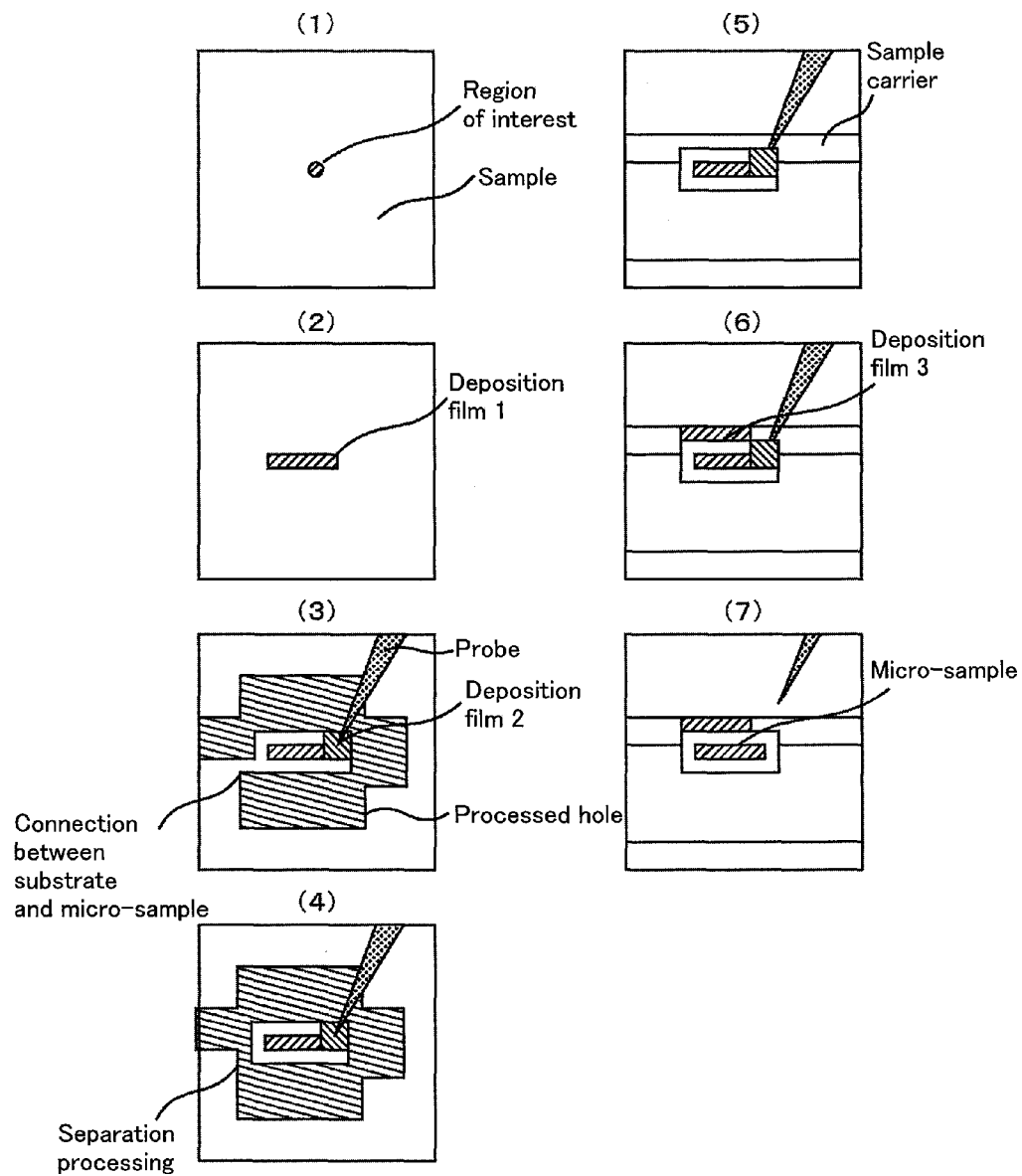
FIG. 8 shows a micro-sampling procedure used in the third embodiment of the present invention.

FIG. 8 illustrates the (micro-sampling) method, implemented in the third embodiment, for extracting from a region to be observed. First, a first deposition film 1 is formed by FIB-induced deposition at the region of interest in the sample 1 which is fixed to the large-sample stage 160. This was performed by supplying tungsten hexacarbonyl gas to the sample surface from the gas source 170, and performing local irradiation with the FIB. Next hole processing was performed. The hole processing was implemented by performing groove processing on the surroundings of the first deposition film 1 and then inclining the sample and performing processing (FIB processing) to form slits at bottom portion. Next, the sample is returned to the original inclination, a tip of a probe (needle), which is attached to a tip of the manipulator 140, is caused to contact an edge of the first deposition film 1, and the first deposition film 1 is bonded to the probe tip by forming a second deposition film 2 using FIB-induced deposition. The connection between the substrate and the micro-sample is then cut by FIB irradiation and the probe is caused to rise so that the micro-sample including the region of interest is extracted. The large-sample stage 160 is then moved so that the thin-film carrier 10 enters the optical axis of the FIB. The micro-sample is then brought into contact with the thin-film carrier 10 and fixed to the thin-film carrier 10 using a third deposition film 3. Thereafter, the second deposition film 2 is removed by FIB irradiation to separate the micro-sample and the probe.

According to this process, the micro-sample which includes the region of interest is transferred from the sample 1 to the carrier.

Figure 10:
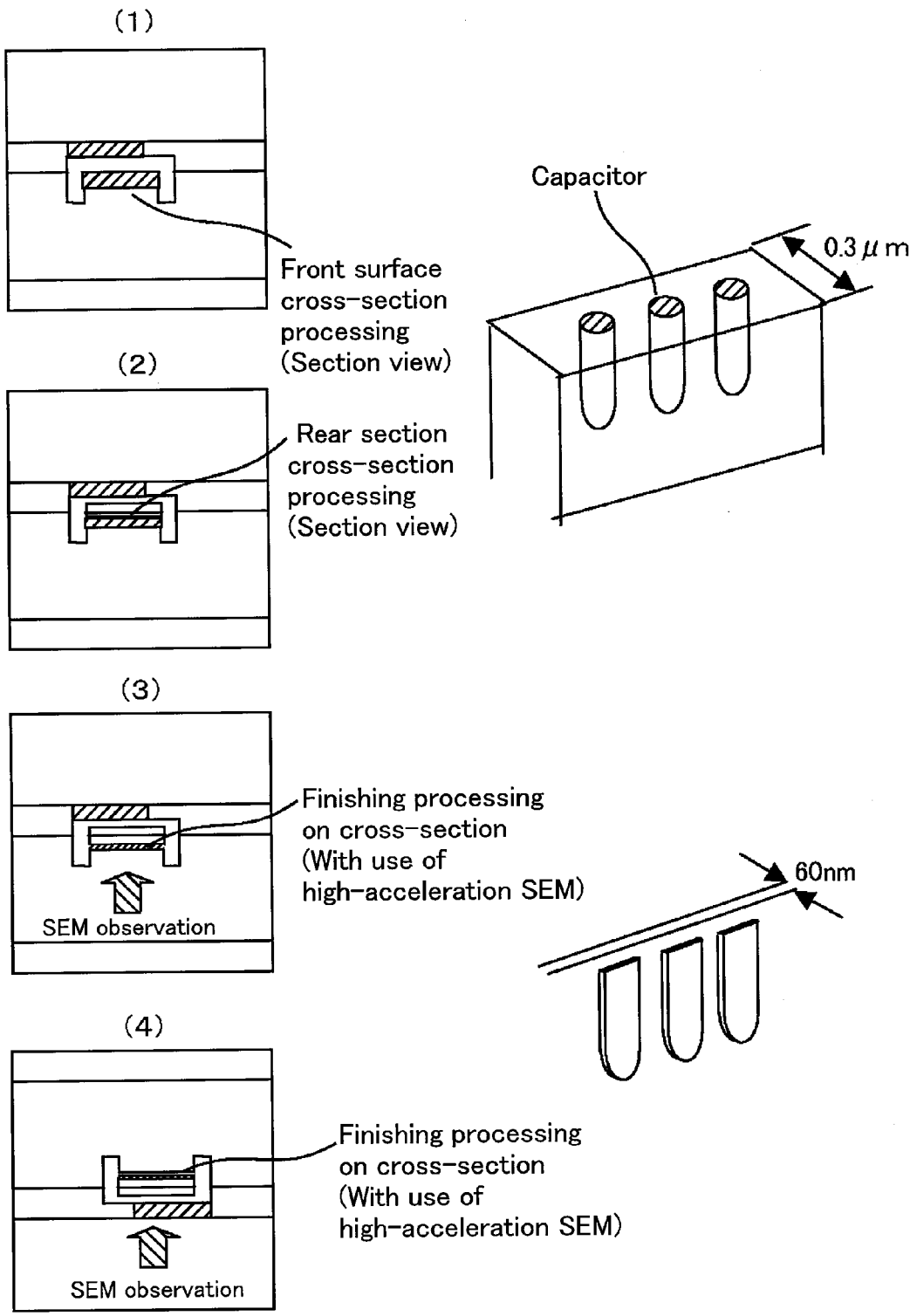
FIG. 10 is a thin film processing procedure used in the third embodiment of the present invention.
Figure 11:
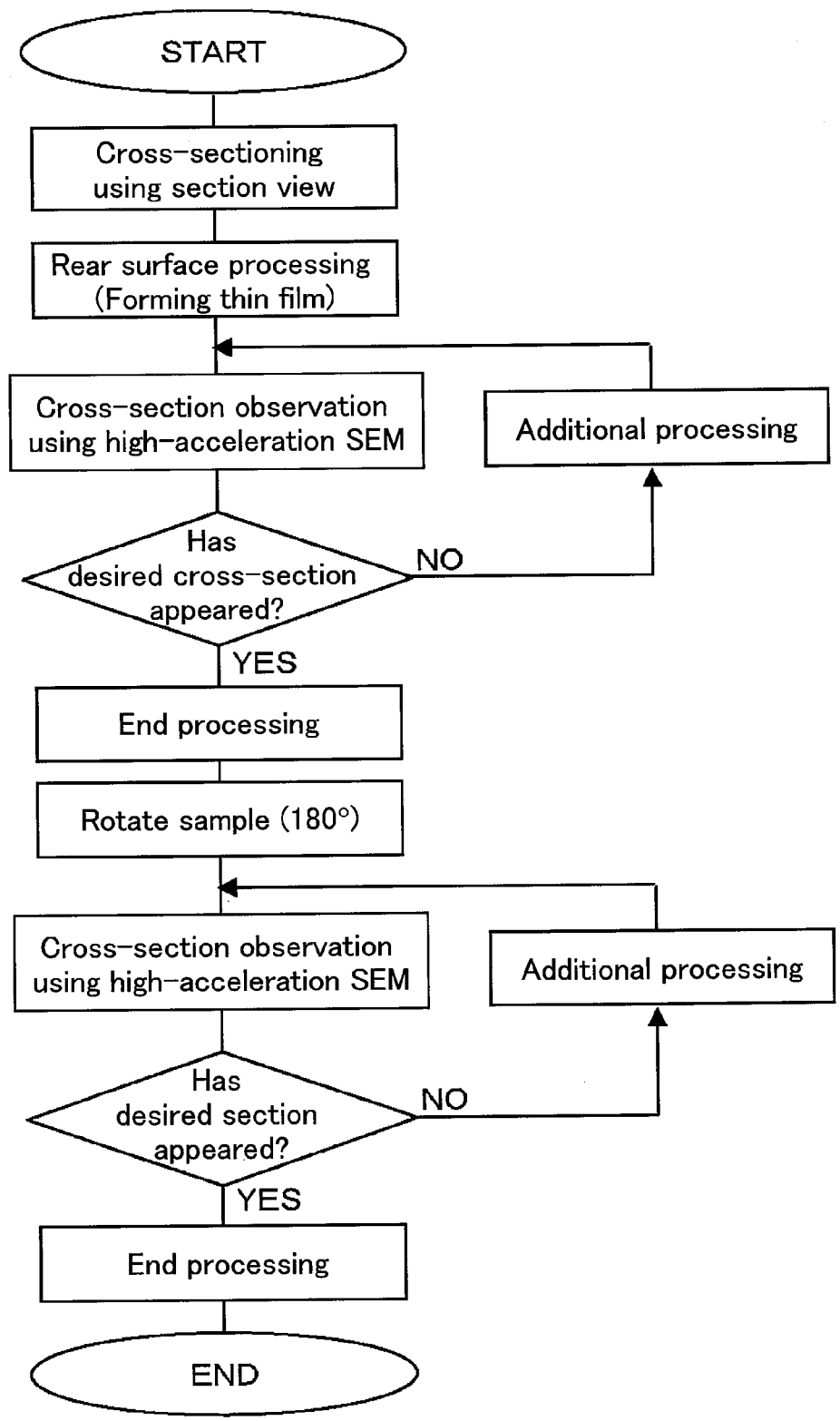
FIG. 11 is a processing flow chart used in the third embodiment of the present invention.

The micro-sample transferred to the carrier is then formed into a thin field using a process shown in FIG. 10. The process to form the thin film is described below with reference the flowchart of FIG. 11.

First, sectioning of the micro-sample was performed using the section view. The region of interest was a capacitor of a semiconductor sample, and the processing was completed when the cross-section at which a neighboring array of capacitors disappeared was found using the section view. A surface on a rear surface side of the sample was processed by setting a processing region that includes the capacitors and having a standard thickness of 0.3 µm, thereby forming the sample into a thin film. The processing of the rear surface can also be performed using the section view. Next, the film thickness was gradually reduced using FIB cross-section processing with the object of producing a section from a central part of the capacitors of interest. The end point of this process was found by checking cross-section information using an SEM with an acceleration voltage of 30 kV. Although the sample was composed of a material, known as a low-k material, which is vulnerable to electron beam irradiation, because the 30 kV electron beam passed through the thin film sample and the loss of energy in the sample was small, damage and deformation in the sample could be minimized.

The sample was then rotated 180°, and processing was performed on the rear surface in the manner described above with the result that a thin film containing a central portion of the capacitor and having a thickness of 60 nm is formed.

Thus, by performing final finishing processing to produce a thin film while checking the section using a high-acceleration electron beam after the thin film processing using of the section view, it is possible to realize thin film processing which minimizes damage and deformation and gives a high level of positional accuracy, even for materials which are vulnerable to damage and deformation by electron beam irradiation. The thin films of each carrier resulting from the processing were then transferred to the high acceleration STEM or TEM holders, and observation of high resolution images was performed.

Fourth Embodiment

Figure 7:
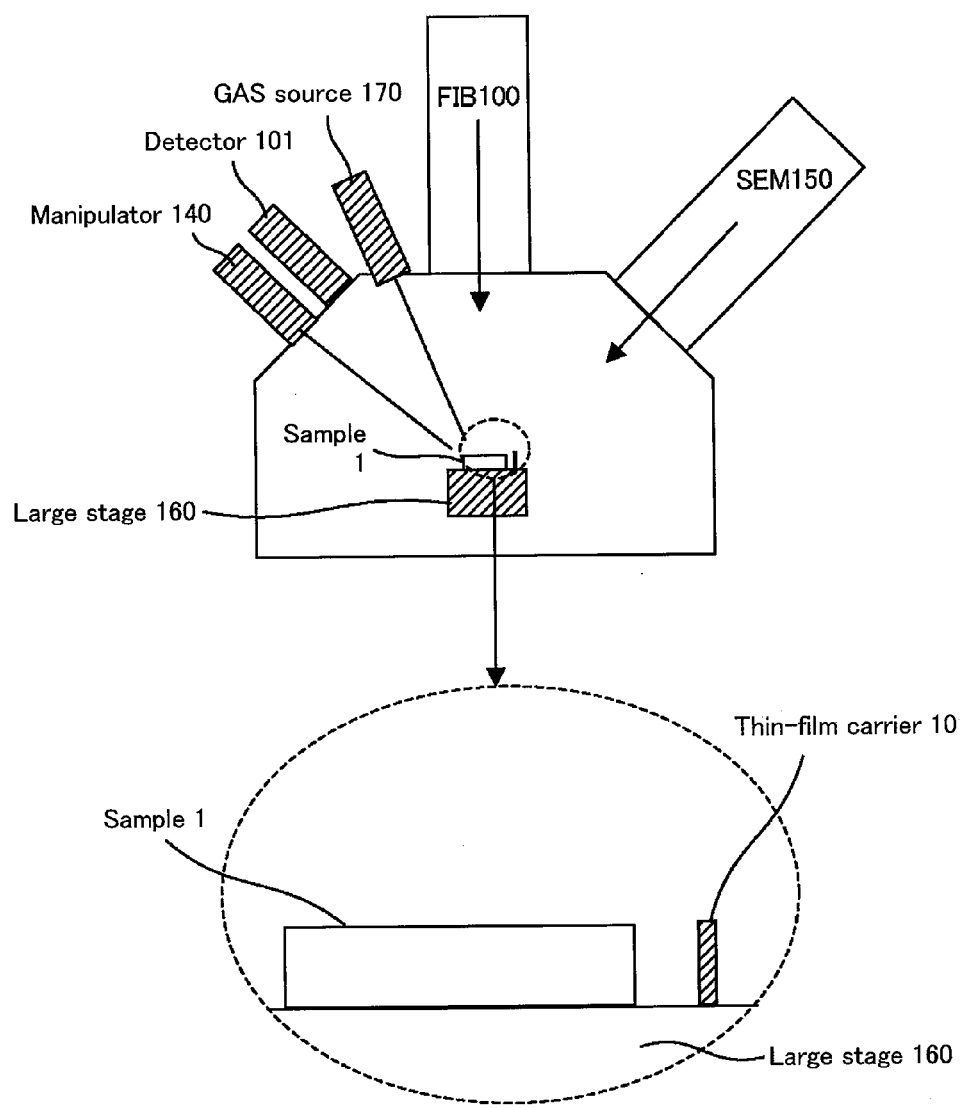
FIG. 7 shows a construction diagram of the FIB-SEM apparatus used in a third embodiment of the present invention.
Figure 12:
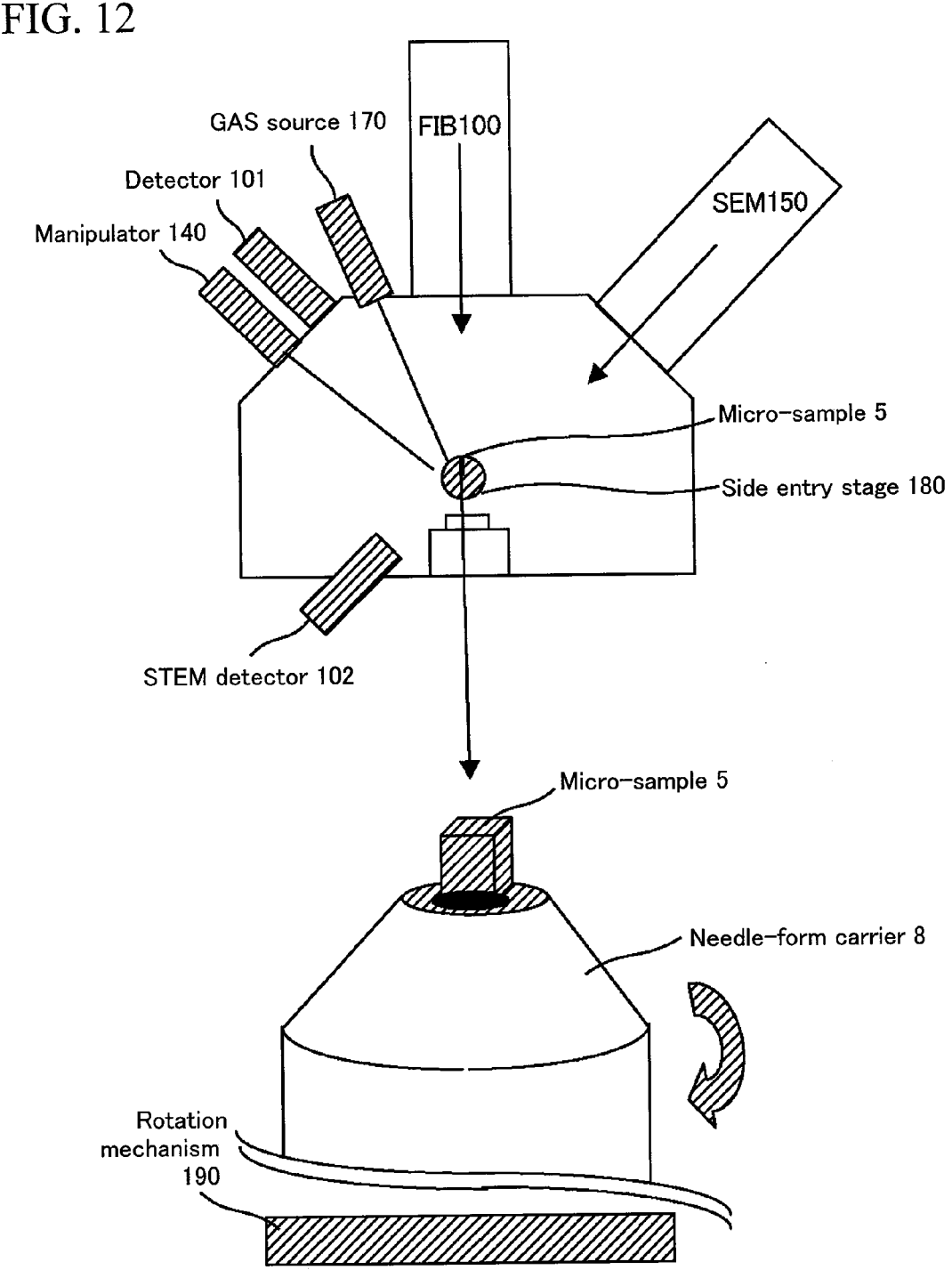
FIG. 12 shows a construction of the FIB-SEM apparatus used in a fourth embodiment of the present invention.

The fourth embodiment is an example in which the cross-section monitoring during the finishing of the thin film is implemented with STEM imaging. The construction of the apparatus is shown in FIG. 12. In the inclusion of an FIB, an SEM and a gas source, the present apparatus resembles that of FIG. 7. However, the present apparatus further includes a side entry stage 180 and a STEM detector 102. A needle-form carrier 8 is mounted on the side entry stage 180, and a holder having mechanism for rotating the needle-form carrier 8 is installed in the side entry stage 180.

Figure 13:
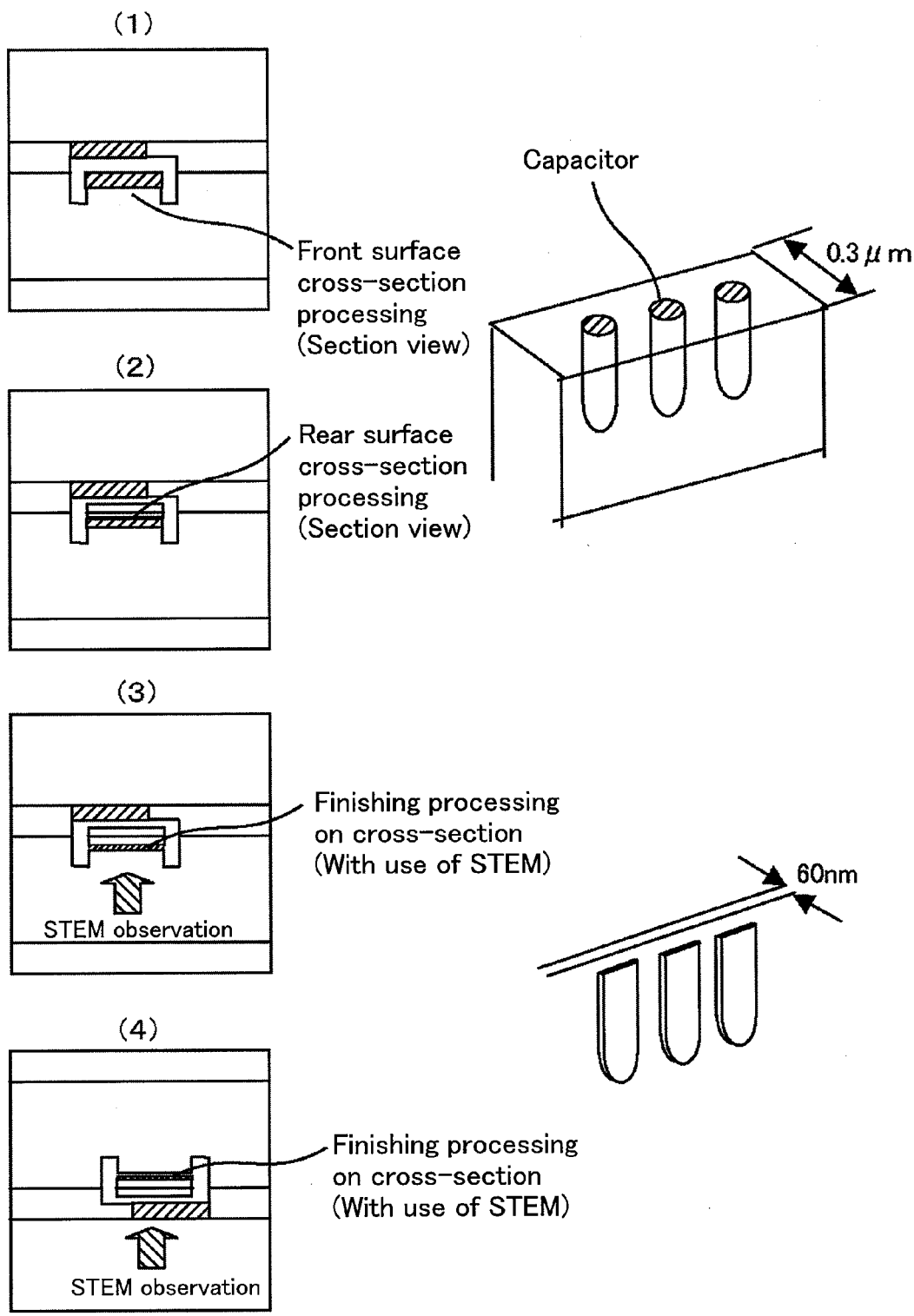
FIG. 13 is a thin film processing procedure used in the fourth embodiment of the present invention.

The micro-sample 5, which has been separated from the sample 1, was fixed using FIB induced-deposition to the tip of the needle-form carrier 8 on the holder installed in the side entry stage 180. The fixed micro-sample was then formed into a thin film using the procedure shown in FIG. 13. The procedure of FIG. 13 resembles the procedure of FIG. 10 but differs in that an STEM is used in the electron-beam observation of the cross-section structure during the finishing processing. The STEM image is captured by detecting an electron beam which passed through the thin film using an STEM detector 102. To proceed from (3) to (4) in the process shown in FIG. 13, it is necessary to rotate the sample. In the present embodiment, the needle form carrier 8 was rotated using the rotation mechanism 190 in the holder.

The micro-sample which has been formed into a thin film is installed in the side-entry holder. It is then possible to perform imaging and observation at even higher resolutions by removing and transferring the holder to dedicated TEM and STEM devices. Since the present embodiment does not require the carrier to be attached and removed once the micro-sample has been installed, the risk of damage or loss to the sample during work on the sample is low. This method is therefore suitable for fault analysis in which it is difficult to secure a plurality of samples.

What is claimed is:

1. A processing and observation apparatus using a focused ion beam, comprising a control apparatus configured to acquire a processing monitor image formed from secondary particles generated from a sample by the focused ion beam that mills a cross-section, the processing monitor image indicating a cross-sectional structure during processing, wherein:

the control apparatus includes a display unit configured to display the acquired processing monitor image, and a first indication region and a second indication region are displayed on the display unit together with the processing monitor image, the first indication region indicating a change in a zoom ratio of the processing monitor image along an x-axis, and the second indication region indicating a change in a zoom ratio of the processing monitor image along a y-axis.

2. The processing and observation apparatus according to claim 1, further comprising an electron beam column.

3. A processing and observation system for a micro-sample, comprising the processing and observation apparatus according to claim 1, and an electron beam apparatus having a high acceleration voltage of 15 kV or above.

\* \* \* \* \*